(12) United States Patent
Cox

(10) Patent No.: US 7,198,486 B2
(45) Date of Patent: Apr. 3, 2007

(54) ROTARY DENTAL FILE HAVING A SAFE BREAKAGE POINT

(76) Inventor: Duane Edward Cox, 1269 Wildcliff Pkwy., Atlanta, GA (US) 30329

( * ) Notice: Subject to any disclaimer, the term of this patent is extended or adjusted under 35 U.S.C. 154(b) by 191 days.

(21) Appl. No.: 10/836,793

(22) Filed: Apr. 30, 2004

(65) Prior Publication Data

US 2005/0244785 A1    Nov. 3, 2005

(51) Int. Cl.
*A61C 5/02* (2006.01)
(52) U.S. Cl. .................. 433/102; 433/165; 433/166
(58) Field of Classification Search ............... 433/102, 433/75, 81, 224, 225, 165, 166
See application file for complete search history.

(56) References Cited

U.S. PATENT DOCUMENTS

| | | | |
|---|---|---|---|
| 4,155,462 A * | 5/1979 | Bendel | 211/151 |
| 4,934,934 A | 6/1990 | Arpaio, Jr. et al. | |
| 5,017,138 A | 5/1991 | Schilder | |
| 5,482,465 A * | 1/1996 | Filhol | 433/225 |
| 5,586,885 A | 12/1996 | Kert | |
| 6,128,966 A * | 10/2000 | Usui et al. | 73/865.8 |
| 6,955,536 B1 * | 10/2005 | Buchanan | 433/27 |
| 2002/0182565 A1 * | 12/2002 | Senia et al. | 433/102 |

* cited by examiner

*Primary Examiner*—Cris L. Rodriguez
*Assistant Examiner*—Patrick J. Kilkenny
(74) *Attorney, Agent, or Firm*—David George Johnson

(57) ABSTRACT

An endodontic file (6) including a discontinuity (18) formed within the file shank (7). The discontinuity (18) creates a safe breakage point at which the file (6) will fail prior to a failure occurring at any other point along the length (11) of the file. The safe breakage point prevents the tip (21) of the file (6) from becoming irremovably embedded in a human tooth (12) after file failure. Substantially the entire length (11) of the file (6) remains connected to the tip (21) after file failure, thereby providing a considerable portion of the file which may be gripped and manipulated in order to accomplish file removal. Empirical data is presented to permit proper characterization of the region surrounding the discontinuity (18).

2 Claims, 5 Drawing Sheets

ROTARY DENTAL FILE HAVING A SAFE BREAKAGE POINT

FIELD OF THE INVENTION

The present invention relates generally to the field of endodontic components used in performing root canal therapy procedures, and more specifically to a rotary endodontic file having a predictable failure or separation point at an optimized location.

BACKGROUND OF THE INVENTION

A rotary dental file is an instrument used to perform a reaming operation during the course of an endodontic procedure. The goal of the procedure is to remove dead or damaged material from the root canal of a tooth prior to filling the excavated canal. Examples of instruments of this kind are referred to in U.S. Pat. No. 4,934,934, entitled "Dental File/Reamer Instrument, issue on Jun. 19, 1990, to Arpaio, Jr. et al. and U.S. Pat. No. 5,017,138, entitled "Set of Endodontic Instruments", issued on May 21, 1991 to Schilder.

In order to use such an instrument, the shank of the rotary file is inserted into the chuck of a dental drilling instrument, or into a handle that may be directly manipulated by a dentist. In operation, an endodontic drill is operated at a speed of approximately three hundred revolutions per minute. This rotary speed achieves the necessary surface velocity for the various protrusions or edges projecting from the file that are adapted to cut, abrade, shape and excavate the root canal of the tooth undergoing the endodontic treatment. The relatively low rotation speed is accompanied by a correspondingly high drive torque that is transferred to the instrument as it rotates along with the chuck.

The surface and the shape of the root canal are irregular. As the surface of the rotary file enters the root canal and encounters the relatively hard canal wall surface, the high driving torque generated by the drill creates the risk that the working part of the rotary file will break off, fracture, or otherwise separate into two pieces. This is especially true for endodontic files made of nickel titanium. File separation typically leaves some part of the rotary file embedded in the root canal. The fracture usually occurs about two millimeters from the file tip. Consequently the embedded, separated file tip is quite difficult to extricate from the tooth. Sometimes the tip can only be removed by a specialist, and in some cases the tip is left in the patient's tooth. Rotary file breakage may occur suddenly and without warning, even with a new file. Breakage can occur regardless of the brand of file, its design, age, length, taper or size.

Past attempts to address the problem of rotary file torsional failure have incorporated the concept of manufacturing an intermediate part of the file shank so as to have a torsional fracture strength that is substantially less than that of the remainder of the file shank. An example of such a device is disclosed in U.S. Pat. No. 5,586,885, entitled "Dental File/Reamer Instrument", issued on Dec. 24, 1996 to Kert. The goal of the Kert arrangement is to place any fracture of the rotary file outside of the root canal, making it possible to remove the embedded portion of the file by gripping the protruding portion. However, the Kert device has not succeeded in clinical practice because the characteristics of the annular groove used to weaken the shank are not disclosed. In particular, the dimensions and shape of the groove are not discussed in sufficient detail to permit precise use on files of different diameters, lengths and tapers. The result is a rotary file that either fractures so readily as to be useless or that does not fracture when needed, resulting in a failure in another portion of the file near the tip prior to the failure of the weakened area.

The result is that rotary file manufacturers have addressed the file breakage problem by focusing on improved endodontic techniques and by encouraging the use of new files for each endodontic procedure. These efforts have not solved this widely recognized and frequently occurring problem.

SUMMARY OF THE INVENTION

The present invention is an improved rotary endodontic file. The present invention utilizes a safe breaking point formed within a file to promote breakage of the file at a known point well outside of the root canal region. The safe breaking point can be formed on the shaft by various means including the formation of a spiral or annular groove, shaft compression, the addition of radial lands and cutting flutes above the normal file cutting and shaping region, weakening of the shaft with a laser, forming single or multiple nicks or notches, drilling a hole within the shaft or forming the shaft so as to have a negative taper in the region near the drill chuck.

The formation of the shank alteration must occur at the appropriate location on the shank. Further, the goal of the shank alteration is to achieve a torque value that will result in reliable shank failure without inducing such failures during normal file usage. The determination of the acceptable range of desired torque values for any given file, as well as the location of the file deformation in order to achieve the range of desired torque values, constitute two of the novel features of the present invention. The result of the proper location and formation of the safe breakage point permits the rotary endodontic file to be used more routinely as a power tool and less as a delicate instrument which is subject to frequent failures even in the hands of a skilled and experienced professional.

DETAILED DESCRIPTION OF THE INVENTION

Figure 1:
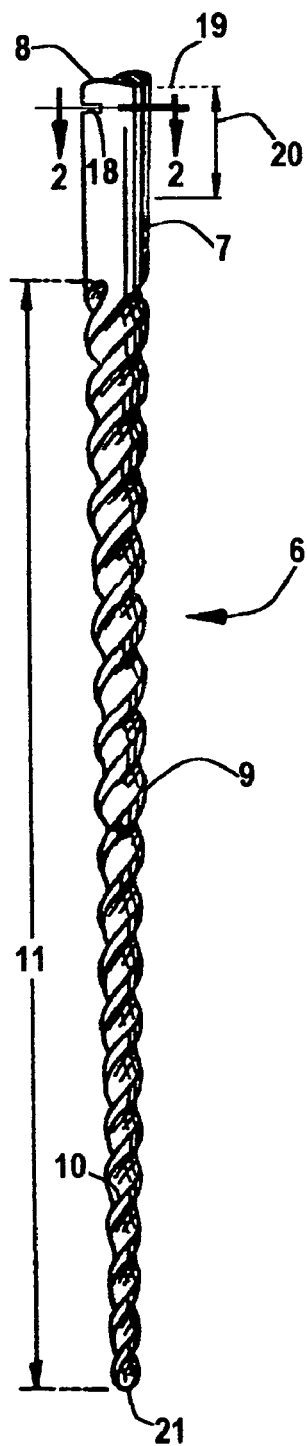
FIG. 1 is a side elevation of a rotary endodontic file constructed in accordance with the principles of the present invention.

Referring to FIG. 1, a rotary endodontic file 6 is illustrated. The file 6 is composed of a metallic material and includes an elongated tapering shank 7. The file 6 is typically fabricated from a nickel-titanium alloy known by the trade name Nitinol or by its scientific formula NiTi. Files composed of nickel-titanium possess superior flexibility, torsional and fracture resistance properties as compared to the previous industry standard stainless steel files. The upper region 8 of the shank 7 is adapted to fit within the chuck employed by a power driven rotary tool, or within a handle designed to be directly gripped by a practitioner as is well known in the art. The lower region 9 of the file shank is formed to include some type of cutting, abrading or shaping protrusion, ridge or edge 10. The length 11 of the lower region 9 typically occupies most of the length of the tapering shank 7.

Figure 3:
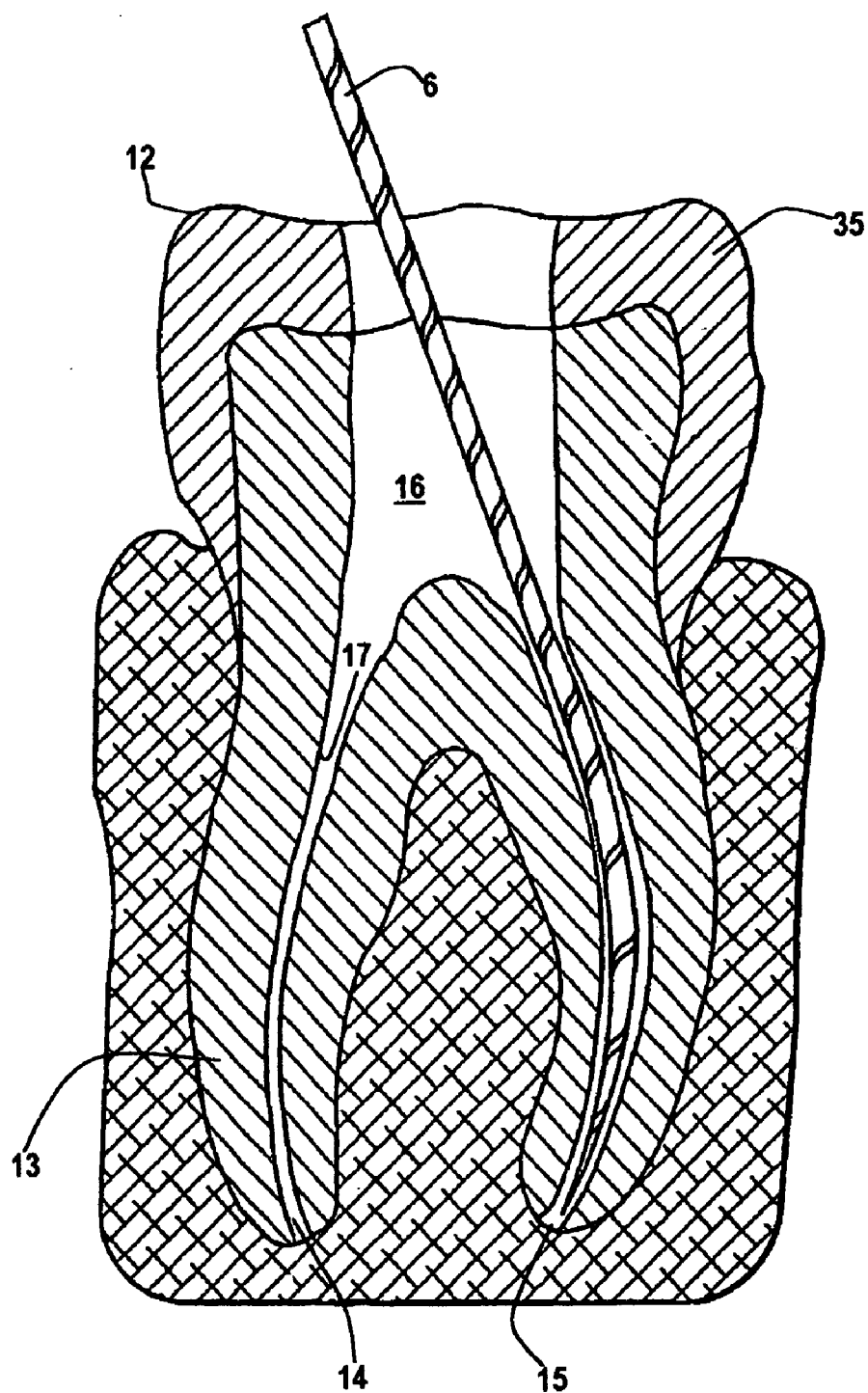
FIG. 3 is a partial cross sectional view of a human tooth.

Referring also to FIG. 3, the use of the rotary file 6 can be understood by viewing the partial cross section of a tooth 12. The tooth 12 includes a supporting root structure 13. Within each root 13 is a channel or root canal 14. The root canal 14 of the tooth 12 houses the circulatory and neural systems of the tooth. These enter the tooth 12 at the tip 15 of each of its roots 13 and extend through the narrow, tapered canal 14 until reaching the pulp chamber 16 that is adjacent to the crown portion 35 of tooth 12. When the pulp tissue becomes diseased or injured the tooth 12 can generate severe pain, sometimes necessitating extraction of the tooth. Root canal therapy involves removing the diseased tissue from the canal 14 and sealing the canal system in its entirety. If successful, root canal therapy can effectively alleviate the pain and hence the tooth need not be extracted.

The first step in performing a root canal procedure is to drill into the tooth 12 and locate the root canal 14. The dentist next uses the rotary file 6 to remove the decayed tissue from the canal 14. The primary goal is to remove all of the decayed material within the canal 14 while leaving the root canal walls 17 relatively unaffected. Preserving the structural integrity of the root canal 14 is important in order to allow proper filling of the root canal and to prevent leakage between the root canal system and the surrounding tissues of the tooth 12. After the diseased material is removed from the root canal 14, it is closed with a sealing material such as gutta-percha which is compressed into the canal 14 by means of a suitable condenser instrument.

The root canals 14 are not necessarily straight and are often curved. Clearing decayed tissue from the canal 14 must be achieved while preserving its original shape. Stainless steel instruments tend to straighten or otherwise alter the natural shape of the canal 14. This problem is exacerbated when the opening of the root canal 14 is small, as often occurs due to calcified deposits on the root canal walls. While the highly flexible nickel-titanium alloy files 6 offer superior flexibility and torsional properties as compared to stainless steel instruments, the nickel-titanium files are more prone to breakage or separation. The solution to the breakage problem is to form a weakened area or discontinuity 18 within the shank 7. The optimum distance 20 between the location of the discontinuity 18 and the plane of engagement 19 at which the handle or chuck grips the shank 7 is in the range of approximately one to two millimeters. The selection of distance 20 within this range preserves enough of the remaining length of shank 7 to permit removal of the shank 7 from a chuck or handle. The portion of the shank 7 extending from the canal 14 is sufficient to permit removal of the shank from the tooth 12. Further, due to the low modulus of elasticity of the nickel-titanium alloy, the tip 21 does not lock tightly into the canal 14.

Figure 2:
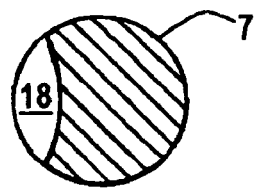
FIG. 2 is a sectional view taken along line 2—2 in FIG. 1.

Referring also to FIG. 2, the dimensions and shape of the discontinuity 18 are critical to the functioning of the present invention. However, these parameters cannot be specified directly for every file. Rather, the optimum torque value that results in failure of the file 6 at the discontinuity 18 can be measured for any given file geometry, and the discontinuity can be fashioned by any convenient means in order to achieve failure at the desired torque value. The discontinuity 18 may therefore take the shape of a notch as shown in FIG. 2, or may be an annular groove, a helical groove, or a simple orifice passing through the shank 7. Weakening of the shank can also be achieved by other means, such as the addition of radial lands or cutting flutes above the normal file cutting and shaping region 11, exposing the region 18 to a laser bean, compressing or pinching the shank 7, or forming the shank 7 to have a negative taper within the two millimeter region defined by region 20

Figure 4:
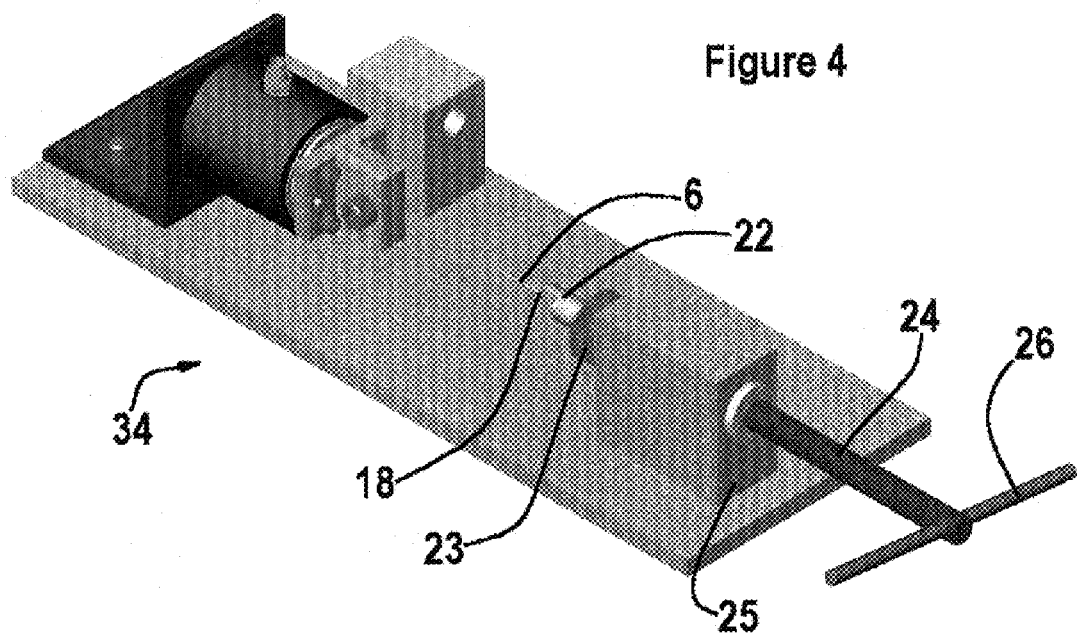
FIG. 4 is a perspective view of a test fixture used for demonstrating characteristics of the present invention shown in a first position.

Referring also to FIG. 4, a test fixture 34 is depicted which permits the determination of torque values as applied to the file 6. Clamp 22 grips the file 6 in a manner simulating the mounting of the file in a conventional drill chuck 23, leaving the discontinuity 18 exposed. The chuck 22 is affixed to an axle or shaft 24 that is supported by a bearing 25. Handle 26 is rigidly affixed to the shaft 24 and permits manual rotation of the shaft 24 and hence the file 6.

Figure 5:
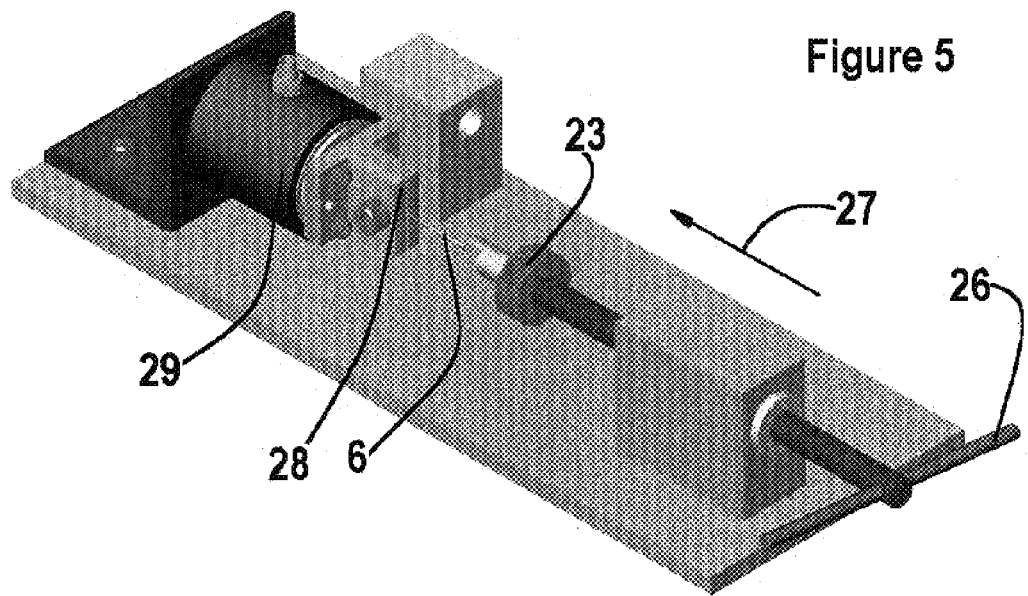
FIG. 5 is a perspective view of a test fixture used for demonstrating characteristics of the present invention shown in a second position.

As seen in FIG. 5, the shaft 24 can be advanced in the direction of arrow 27, permitting the file 6 to be securely gripped by vise 28. The vise is attached to a torque measuring instrument 29 that resists rotation of the file 6 that is induced by rotary manipulation of the handle 26. The file 6 may be rotated until the file separates, and the torque value associated with this failure can be recorded. The nature of the discontinuity 18 may be altered to achieve a torque value that permits the file 6 to perform useful work while failing at the location of the discontinuity prior to a file failure at any other location.

Figure 6:
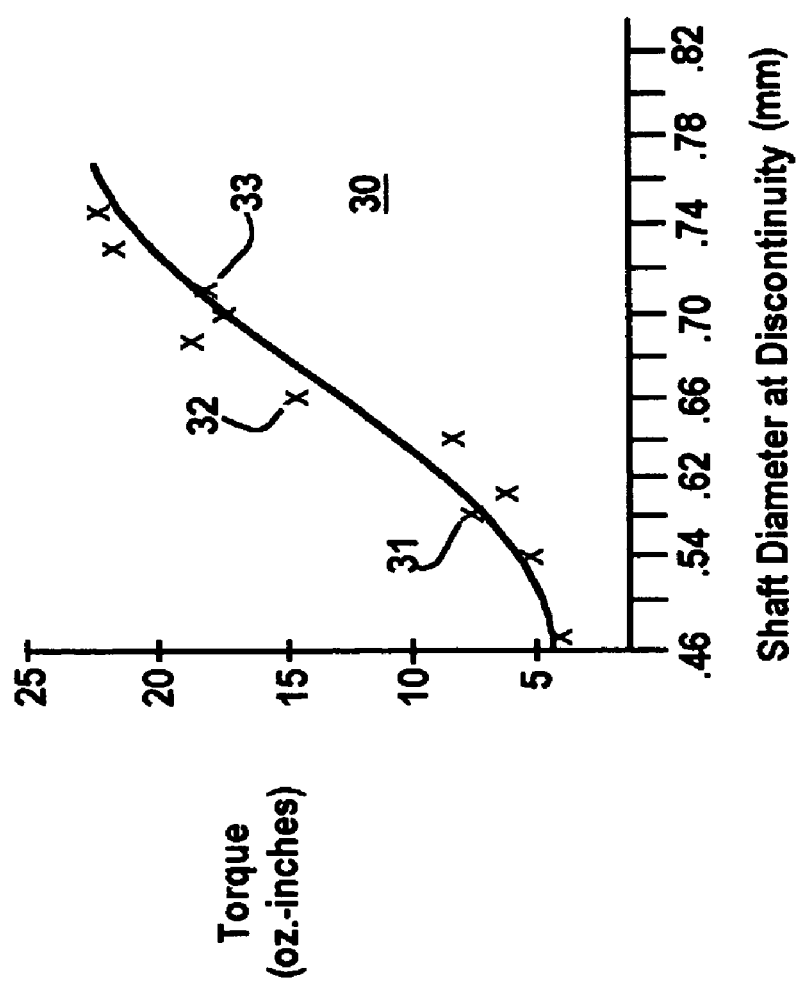
FIG. 6 is a graph depicting the torque values associated with file failures occurring at the safe breakage point created according to the principles of the present invention.

Referring also to FIG. 6, the relationship between the size of the discontinuity 18 and the torque value that causes the failure to occur is depicted. The particular file tested in order to produce the graph 30 is a Series 29, size 30 file having a length of 21 mm and a taper of 0.04, manufactured by the Tulsa Dental Company of Tulsa, Okla. For each file tested in the fixture 34 without the presence of discontinuity 18, the tip 21 will fail at some torque value for any given file diameter. The presence of the discontinuity 18 must therefore induce a failure of the file 6 to occur at the discontinuity 18 at a lower torque value, meaning that the discontinuity 18 must leave a remaining diameter of shank 7 which is less that the diameter which supports a torque value that permits fracture or separation of the file 6 in the region of tip 21. Table I depicts an example of data gathered for a given file, and demonstrates that the remaining diameter of shank 7 should not exceed 0.57 mm in order to prevent file deformation and tip failure while insuring a reliable failure at discontinuity 18.

TABLE I

| Remaining Diameter of Shank 7 (in mm) after Formation of Discontinuity 18 | Condition of File 6 after Application of Excessive Torque |
| --- | --- |
| 0.54 | Separation at discontinuity |
| 0.55 | Separation at discontinuity |
| 0.57 | Separation at discontinuity |
| 0.58 | File deformed |
| 0.59 | File deformed |
| 0.60 | File deformed |
| 0.62 | File deformed |
| 0.63 | File deformed |
| 0.64 | File deformed |
| 0.66 | File deformed |
| 0.67 | File deformed |
| 0.68 | Separation at discontinuity |
| 0.69 | Failed 2 mm from tip 21 |

The various data points 31, 32 and 33, for example, illustrate that larger diameters remaining after the formation of discontinuity 18 within shank 7 require larger torque values to induce a failure, which is a natural result of the greater cross sectional area of the larger diameter shank 7. The curve 30 demonstrates that for any given file diameter that remains after the formation of discontinuity 18, there is an optimum torque value at which the discontinuity will fail. For example, for a file diameter of approximately 57 mm, the torque value at which the file 6 should fail is approximately seven ounce-inches. In other words, if the discontinuity 18 induces failure at the optimum torque value, the file 6 will not fail at or near the tip 21 at a higher torque value. A curve 30 must be constructed for each particular file and discontinuity corresponding to each desired size and geometry in order to identify the optimum torque value associated with that particular file.

While the characteristics of the discontinuity 18 may be determined empirically, another novel aspect of the present invention is a formula to create a file specific safe breakage point 18 regardless of the particular design or manufacturer of the file. Virtually all real world dental files conform to some standards. For example, a size 30 file having a 0.04 taper defines the file 6 as being twenty hundredths of a millimeter in diameter at the tip 21. The taper specification indicates that the file diameter increases by four percent over the tip 21 diameter as one travels in the direction of the shank 7.

In order to create a functional safe breakage discontinuity 18, the diameter of shank 7 must be reduced to the value of the file diameter at a distance of four millimeters from the file tip 21. Thus, for a size 20 file having a 0.04 taper, the effective diameter of the shank 7 in the region of the discontinuity 18 is approximately 0.36 millimeter. Stated for the general case, the formula is:

$$SBP = (TS) + (T * V), \text{ where}$$

SBP is the effective diameter, in millimeters, of the shank 7 in the region of discontinuity 18;

TS is the diameter of tip 21, in millimeters;

T is the taper of the file 6; and

V is a variable that must be determined empirically due to variations in file configurations and uncertain characteristics of root canal 14. The test fixture 34 is used with a hydrated extracted human tooth 12 placed in the clamp 22. The canal 14 is accessed and prepared along its entire length with a No. 10 hand file having a 0.02 taper. A discontinuity 18 is formed in the particular file 6 for which the safe breakage point is to be determined, and the file 6 is overstressed until deformation of the file or file separation occurs. This process is repeated until an optimum value for the shape and dimensions of discontinuity 18 is determined for the particular geometry of a specific file 6.

While the foregoing description describes the preferred embodiment of the present invention, many obvious modifications may be made by those having skill in this field of endeavor. The true scope of the present invention is defined solely by the appended claims.

What is claimed is:

1. A dental file employed by a dentist while performing a root canal procedure, comprising a shaft including:

(a) a shank region, the shank region being adapted to engage a rotary power tool;

(b) an abrading region, the abrading region residing on at least some portion of a surface of the shaft, the abrading region being characterized by a first taper that tapers from a relatively large dimension adjacent to the shank region to a first relatively narrow region adjacent to a tip region of the file, the tin region being oppositely disposed from the shank;

(c) a discontinuity, the discontinuity being formed within a portion of the shank, the discontinuity being shaped and dimensioned so as to cause the shank to separated from the abrading region when a portion of the abrading region becomes embedded in a human tooth and prior to plastic deformation of the file; and (d) an effective diameter, the effective diameter being a relatively smallest dimension of the shank region after formation of the discontinuity that is defined according to the formula:

$$SBP = (TS) + (T * V), \text{ where}$$

SBP is the effective diameter, in millimeters, of the shank region remaining after formation of the discontinuity, the SBP thereby being a specific value in the range of 0.46 to 0.82 millimeters;

TS is a relatively smallest diameter of the tip region of the file in millimeters;

T is the first taper of the abrading region, wherein the taper is a percentage of file diameter change for a change in length of the shank region; and V is a variable having a value determined empirically for the file.

2. A dental file according to claim 1, wherein a first value of torsional force causes the file to fall near the tip region; and a second value of torsional force causes the shank to fail, the first value of torsional force being greater than the second value of torsional force.

* * * * *